(12) United States Patent
Kesling et al.

(10) Patent No.: US 6,682,345 B2
(45) Date of Patent: Jan. 27, 2004

(54) ORTHODONTIC BRACKET

(75) Inventors: Christopher K. Kesling, LaPorte, IN (US); Peter C. Kesling, LaPorte, IN (US); Richard C. Parkhouse, Gwynedd (GB)

(73) Assignee: TP Orthodontics, Inc., Westville, IN (US)

( * ) Notice: Subject to any disclaimer, the term of this patent is extended or adjusted under 35 U.S.C. 154(b) by 0 days.

(21) Appl. No.: 10/177,951

(22) Filed: Jun. 21, 2002

(65) Prior Publication Data

US 2003/0180678 A1 Sep. 25, 2003

Related U.S. Application Data

(63) Continuation-in-part of application No. 10/106,406, filed on Mar. 25, 2002, now abandoned.

(51) Int. Cl.$^7$ ................................................ A61C 3/00
(52) U.S. Cl. ............................................. 433/8; 433/16
(58) Field of Search ......................... 433/8, 9, 10, 11, 433/13, 14, 15, 16, 17

(56) References Cited

U.S. PATENT DOCUMENTS

| | | | | |
|---|---|---|---|---|
| 2,230,315 A | * | 2/1941 | Winslow | 433/11 |
| 3,178,822 A | * | 4/1965 | Fogel et al. | 433/15 |
| 3,218,714 A | | 11/1965 | Wallshein | |
| 3,724,074 A | | 4/1973 | Wallshein | |
| 4,573,913 A | * | 3/1986 | Creekmore | 433/17 |
| 4,842,512 A | * | 6/1989 | Kesling | 433/8 |
| 4,842,514 A | | 6/1989 | Kesling | 433/21 |
| 4,877,398 A | * | 10/1989 | Kesling | 433/16 |
| 5,125,832 A | * | 6/1992 | Kesling | 433/16 |
| 5,374,187 A | * | 12/1994 | Vashi | 433/17 |
| 6,368,105 B1 | | 4/2002 | Voudouris et al. | 433/10 |

OTHER PUBLICATIONS

TP Orthodontics, Inc. Product Catalog, 1998, p. 32.

* cited by examiner

Primary Examiner—Cary E. O'Connor
(74) Attorney, Agent, or Firm—Lloyd L. Zickert

(57) ABSTRACT

An improved orthodontic bracket including a horizontally opening archwire slot for a main aligning archwire for allowing crown tipping, limiting root uprighting, and controlling torquing, and a relatively small horizontal uprighting slot, tunnel or lumen extending substantially mesiodistally for receiving an additional small wire for uprighting teeth and eliminating the need to use individual uprighting springs in the final stage of patient treatment.

41 Claims, 4 Drawing Sheets

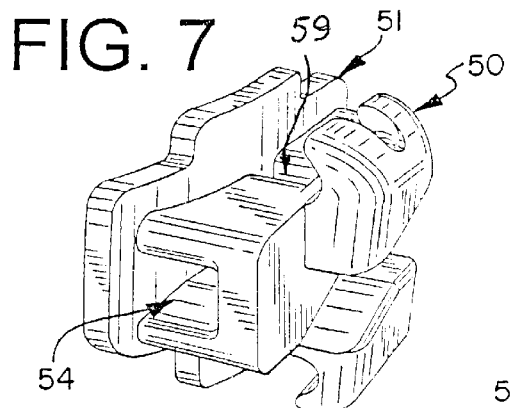
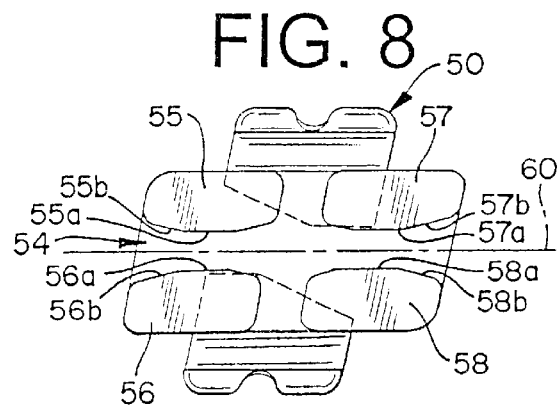
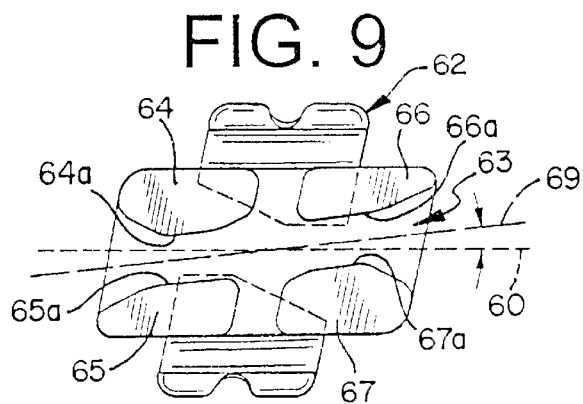
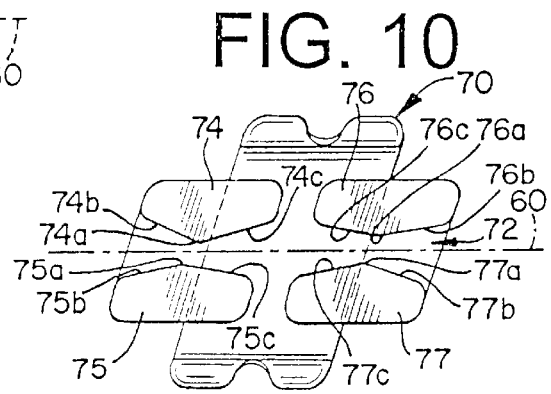
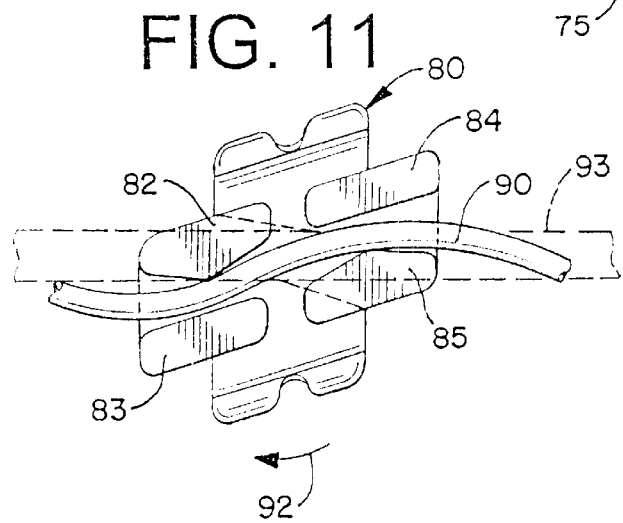

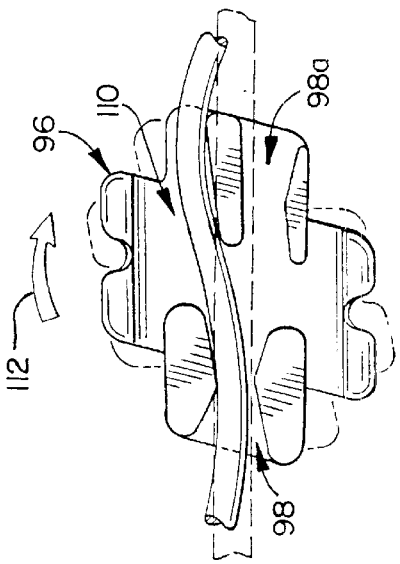
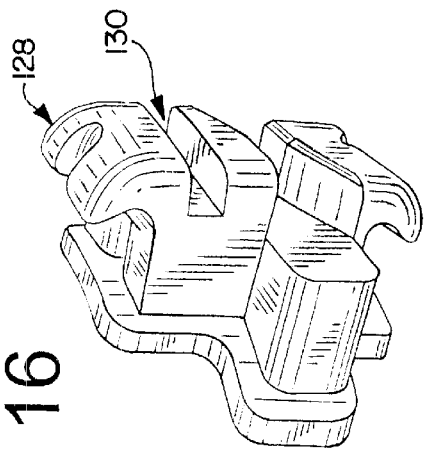

ORTHODONTIC BRACKET

DESCRIPTION

This application is a continuation-in-part of Application No. 10/106,406, filed Mar. 25, 2002, now abandoned.

This invention relates in general to a new and improved orthodontic bracket to be used in conjunction with other brackets on centrals, laterals, cuspids and bicuspids for uprighting teeth without the need for mounting uprighting springs, and more particularly for an improved bracket having means for allowing crown tipping, root uprighting, and torquing functions and which includes means for producing the final uprighting function without the use of individual uprighting springs.

BACKGROUND OF THE INVENTION

Heretofore it has been known to provide orthodontic brackets having means for accommodating crown tipping functions, root uprighting functions, and torquing functions, as disclosed in U.S. Pat. Nos. 4,877,398 ('398) and 5,125,832 ('832). Such a bracket is made and sold by TP Orthodontics, Inc. of Westville, Ind. (TP), under the registered trademark TIP-EDGE, owned by TP Orthodontics, Inc. While these brackets may receive round or rectangular wire, they are designed to perform torquing functions with rectangular wire, and it is preferred that rectangular wire be used in the later stages of treatment.

Further, the brackets above referred to include vertically extending slots or openings for receiving the tails of uprighting springs to perform a root uprighting function. It should be appreciated that it is well known that the vertically extending openings may also receive the tail of a rotating spring for performing a rotating function or a pin for hooking a ligature. U.S. Pat. No. 4,842,514 discloses a type of uprighting spring that may be used with brackets having vertical openings.

It has also been known to provide an orthodontic bracket having a pair of contiguous labiobuccally opening archwire slots, one of which allows tipping and uprighting movements and the other of which provides torquing movement, as disclosed in U.S. Pat. No. 4,842,512. It has also been known to provide a bracket having a pair of contiguous archwire slots, one of which allows crown tipping, limits root uprighting, and controls torquing, while the other slot functions to stabilize tooth movement in three dimensions, as sold by TP Orthodontics, Inc. of Westville, Ind., and illustrated in TP's 1998 Product Catalog.

SUMMARY OF THE INVENTION

The improved orthodontic bracket of the present invention overcomes the need to use uprighting springs for final finishing with a system using brackets having an archwire slot like the brackets in the above '398 and '832 patents to apply root uprighting and/or tipping forces and torquing forces to teeth, as well as the need for selectively mounting such springs to apply such root uprighting and/or tipping forces by additionally incorporating a generally horizontal uprighting lumen or tunnel/opening for receiving an uprighting wire. As to the archwire slot in the bracket of the present invention that allows crown tipping, the '398 and '832 patents are incorporated by reference. Further, the bracket of the present invention reduces the need for individual uprighting springs and therefore also the possibility of improperly mounting such springs during the course of treatment.

The improved orthodontic bracket of the present invention, while having a horizontally opening archwire slot formed to permit mesial-distal crown tipping and to limit root uprighting, includes an additional mesiodistally extending generally horizontally directed tunnel, opening or lumen for receiving a relatively small, super-elastic archwire or a high-tensile uprighting wire that is threaded through similar horizontal openings in adjacent brackets. The horizontal tunnels, tubes, or lumens do not connect into the main archwire slots of the brackets. The tunnels extend generally parallel to the occlusal of the arch on which the brackets are mounted. So, when the patient enters the final stage of treatment and all of the extraction spaces, if any, are closed, the crowns of the teeth may be tipped mesially or distally and in some cases also labially or lingually by threading an uprighting wire through the tubes, wherein the energy of the wire uprights the brackets/teeth.

While the preferred means of attaching the uprighting wire to the bracket is the insertion into a tunnel or lumen, it must be realized that the uprighting wire could be inserted into an open horizontally facing slot. This uprighting slot or lumen could be located in the face of the bracket either gingival or occlusal to the archwire slot.

The slot or lumen could be horizontal wit the occlusal plane so that the uprighting wire would become passive and its forces drop to zero when all the teeth have been uprighted. The slot or lumen could also be angled relative to the horizontal axis of the archwire slot to facilitate engagement of the uprighting wire when the tooth is tipped or to insure a greater initial force, or a continued force after the tooth has been uprighted to the tip and/or torque limits programmed into the horizontal stops within the archwire slot.

The advantage of an open uprighting slot on the labial face of the bracket over a lumen would be in the ease of insertion. Some disadvantages would be the need for retention via a self-locking feature or the use of a ligature, lack of positive engagement and inferior rotational control.

Also, when the uprighting wire is located above or below the plane of the main archwire, whether in a tunnel or a slot, it could interfere with desired changes in the labial-lingual inclination or torquing of the teeth.

The relatively small, super-elastic or high-tensile uprighting wire traveling through the uprighting slots or tunnels are generally substantially continuous, but may be segmented, and may extend from one end of the dental arch to the other end or a section thereof. Thus, the small and continuous or segmented wire can be threaded through the tunnels in the brackets, as well as the tubes of the molars if indicated, in the final stage. Subsequently, the main archwire is placed in the horizontally opening archwire slots, and retained in the slots with suitable ligatures such as elastomeric rings, or a removable cap as used with self-ligating brackets.

An uprighting tunnel, opening or lumen may be continuous or segmented, and may be formed by a plurality of segmental members. Further, a tunnel may be angled in relation to the occlusal plane or have at one end a plurality of paths for selective use depending on the degree of tipping or uprighting required.

Barring any damage to the system, the patient then need not return for a subsequent visit for approximately two to three months, after which time depending upon the initial degree of tipping of the teeth, the roots may be properly uprighted. If further uprighting is required, a larger size wire or higher tensile wire can be threaded through the tunnels or placed in the uprighting slots in the faces of the brackets to complete uprighting. Once the desired uprighting has been accomplished, the appliances may then be removed for the subsequent placement of suitable retainers.

The use of a super-elastic or high-tensile wire in the openings results in the elimination of the need for uprighting springs, and produces greater comfort in the mouth of the patient. The hygienic conditions of the mouth are improved by the absence of the springs which can harbor food particles. Further, the elimination of uprighting springs enhances the aesthetics of the system, and prevents the possibility of selecting an incorrect uprighting spring resulting in applying a force in the wrong direction.

It is therefore an object of the present invention to provide a new and improved orthodontic bracket that eliminates the need for uprighting springs in the final stage of patient treatment, and that additionally makes it impossible to apply undesired uprighting forces that could be applied by inserting the incorrect uprighting spring.

A further object of the present invention is in the provision of an improved orthodontic bracket having a horizontally extending continuous or segmented tunnel, tube, or slot through which a relatively small, super-elastic or high-tensile uprighting wire may be threaded for applying root uprighting forces to teeth, thereby eliminating the necessity to use uprighting springs, and which improves mouth hygiene, reduces patient visits, and improves patient comfort.

Another object of the present invention is to provide a new and improved orthodontic appliance having either an uprighting lumen disposed lingually of an archwire slot that controls tipping, uprighting and torquing, or an uprighting lumen or slot disposed above or below the archwire slot.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 7 is a perspective view of a modification of the invention;

FIG. 8 is a lingual elevational view of the bracket of FIG. 7 with the base removed for purposes of clarity in viewing the tunnel;

FIG. 9 is a lingual elevational view of a modification of the bracket of FIG. 8, wherein the tunnel is offset from the horizontal;

FIG. 10 is a lingual elevational view of a further modification of the invention, wherein the tunnel is formed by mesiodistally spaced apart opposed knife-edge members;

FIG. 11 is a lingual elevational view of a further modification of the invention, wherein the segmented tunnel is formed by a pair of members, one of which has a flat surface and the other of which has a knife-edge and also showing the bracket in a tipped position and the flexed uprighting wire threaded through the tunnel;

FIGS. 12 to 14 are lingual elevational views of a further modification of the invention and showing sequentially the coaction between the uprighting wire and the tunnels and the resulting movement, wherein the uprighting wire is threaded through the lower path initially, for ease of insertion, as shown in FIG. 12, and then through the upper path to reactivate the uprighting wire and continue uprighting, as shown in FIGS. 13 and 14;

FIG. 15 is a side elevation view of a modified bracket according to the invention showing lumens aligned above and below the archwire slot; and FIG. 16 is a perspective view of a further modified bracket showing an uprighting slot on the bracket face for receiving an uprighting wire.

DESCRIPTION OF THE INVENTION

The improved bracket of the invention eliminates the need to use uprighting springs in the final stage of orthodontic treatment when using the well known Tip-Edge brackets which include archwire slots that permit crown tipping functions, root uprighting functions, and torquing functions, as disclosed in the brackets of the above-mentioned U.S. Pat. Nos. 4,877,398 and 5,125,832. These brackets in a system may be fitted with a main round archwire in early stages of treatment but are usually fitted with a main rectangular archwire in later stages of treatment.

Figure 1:
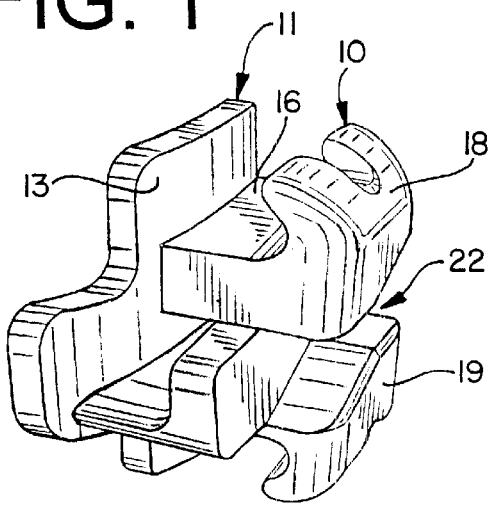
FIG. 1 is a perspective view of the improved bracket of the invention.
Figure 3:
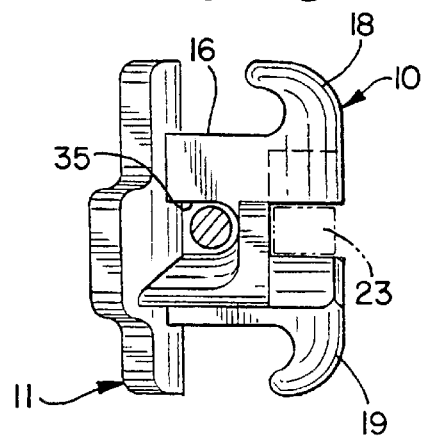
FIG. 3 is a side elevational view of the bracket of FIGS. 1 and 2 and taken generally along line 3—3 of FIG. 2.
Figure 2:
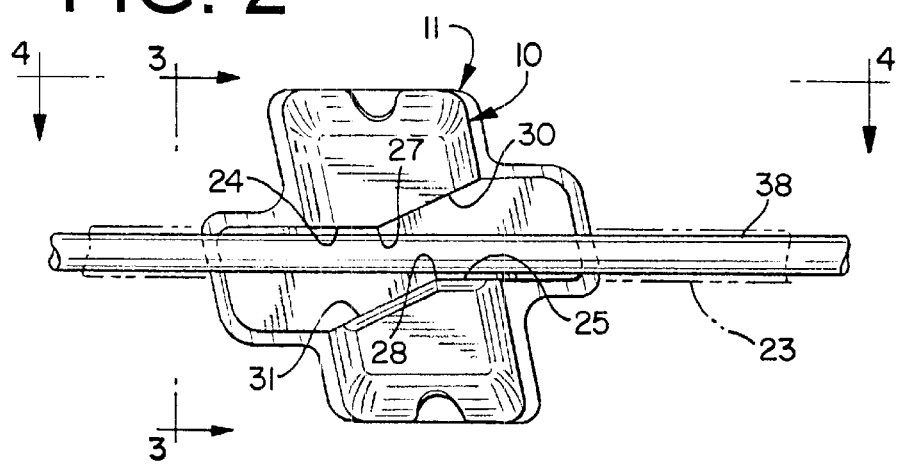
FIG. 2 is a front elevational view of the bracket of FIG. 1 and showing in phantom the main archwire disposed in the archwire slot and the uprighting wire disposed in the horizontal tunnel or tube and with the ligature or retentive cap removed for purposes of clarity.
Figure 4:
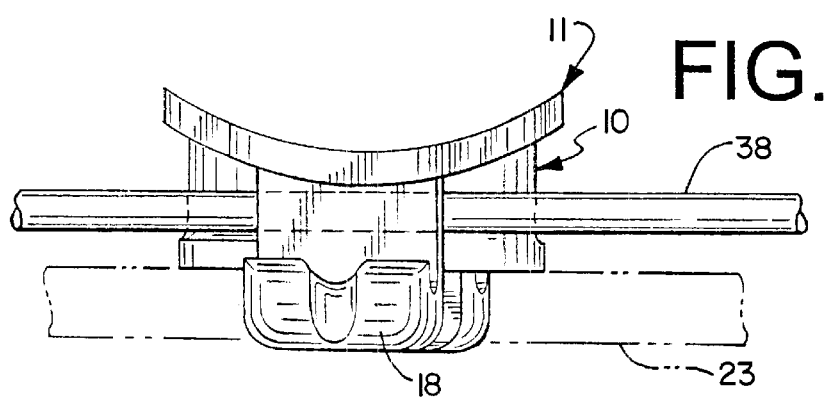
FIG. 4 is a top elevational view of the bracket of FIGS. 1 to 3 and taken generally along line 4—4 of FIG. 2.
Figure 5:
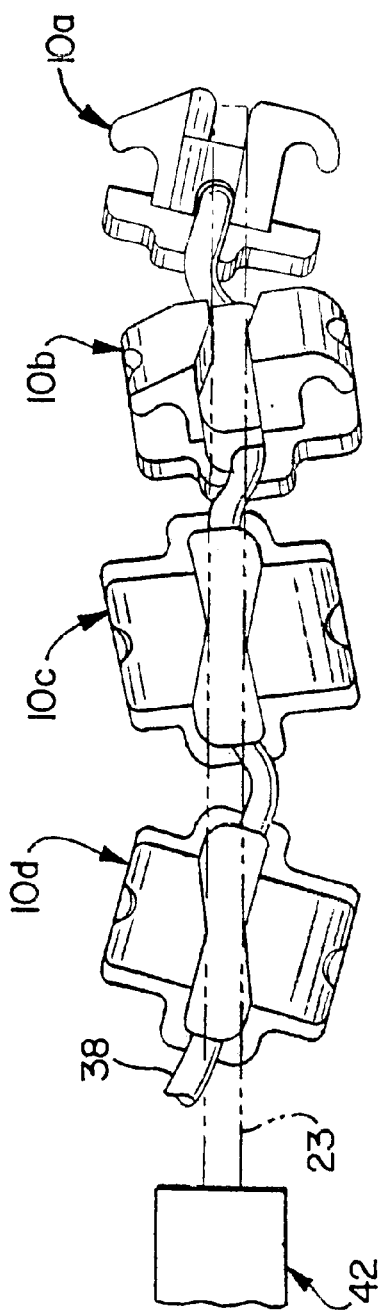
FIG. 5 is a view of a system along the right side of the mandibular arch illustrating a plurality of brackets, a flexed uprigining wire in solid and a main archwire in phantom as they would appear initially with the teeth tipped as the patient goes into the final stage of treatment; although ligatures or caps for retaining the main archwire in the slots of the brackets are omitted for purposes of clarity.
Figure 6:
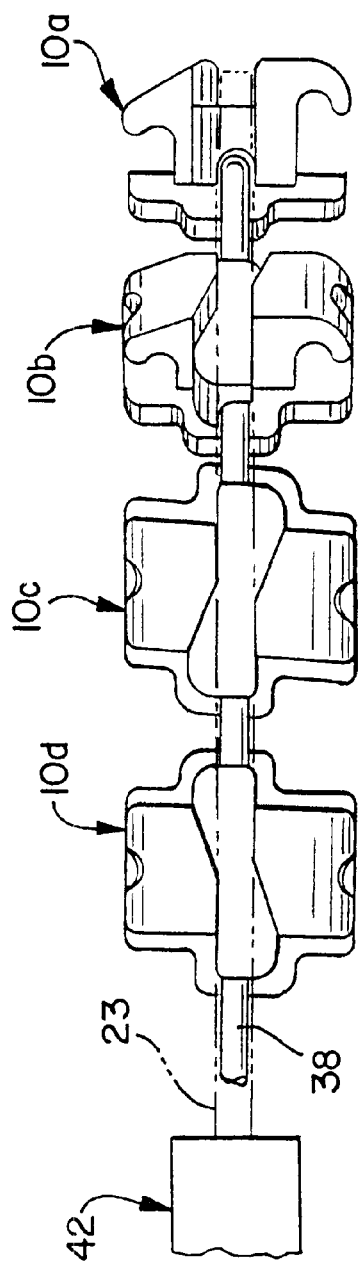
FIG. 6 is a view similar to FIG. 5 but illustrating the brackets as positioned after the teeth have been uprighted following the forces being delivered by the uprighting wire extending through the horizontal tunnels or tubes of the brackets.

It has also been known in the use of such brackets in a system that as a patient enters the final stage of treatment and all extraction spaces are closed and the crowns of teeth are tipped mesially or distally and in some cases also labially or lingually, as illustrated generally in FIG. 5. Heretofore, individual uprighting springs have been applied to the brackets to produce clockwise or counter-clockwise forces to bring the brackets and their respective teeth into their final upright positions. The upright positions desired are generally illustrated in FIG. 6. For purposes of clarity, the brackets illustrated in FIGS. 5 and 6 are not shown as being mounted on teeth, and no ligatures or caps are shown for retaining the main archwire in the open bracket slots. This system also presumes that the brackets would be mounted on centrals, laterals, cuspids and bicuspids, although it will be appreciated that this system will be applicable for the mouth of any individual patient and may have more or less brackets.

Referring now to the drawings, and particularly to FIGS. 1 to 4, the bracket of the invention, generally designated by the numeral 10, is shown as mounted on a bonding base or pad 11. It would be appreciated that the bracket and base may be made in one piece if desired.

The base 11 includes an outer face 13 to which the bracket 10 is suitably attached. It will be appreciated that the base as shown is arcuately formed to generally conform to the labial surface of a tooth when the bracket and base are bonded to the tooth in the usual manner. As above mentioned, these brackets would be mounted on the centrals, laterals, cuspids and bicuspids of a patient.

The bracket 10 includes a body 16 having upper and lower tie wing tips 18 and 19 between which is formed the main archwire slot 22 of the bracket. However, it should be appreciated that the bracket may not have wings, particularly if it is of the self-ligating type. As particularly seen in FIG. 2, the archwire slot 22 is somewhat propeller shaped and includes upper and lower parallel, planar root uprighting stops or walls 24 and 25 which coact to limit the uprighting position of the bracket and respective tooth to the ideal position during uprighting. The stops also define a height compatible with the height of a rectangular archwire, so that following uprighting, the archwire is fully engaged by the stops to produce torquing forces. The stops 24 and 25 are generally diagonally opposed from one another and merge at diagonally disposed fulcrums 27 and 28 with crown-tipping surfaces or walls 30 and 31. The horizontal axis of the slot parallels the stops. These surfaces are generally opposite to the root uprighting stops and allow crown tipping functions.

In order to accommodate an uprighting wire according to the invention, a horizontally extending uprighting tunnel, lumen or opening 35 is defined by the base 11 and a slot in the body 16 directly lingual to and in general alignment with the uprighting stops or walls 24 and 25 of the archwire slot 22. It will be appreciated the uprighting lumen may be formed in the main body of the bracket or in conjunction with or in the bonding base or pad. When mounted on a tooth, the tunnel would extend substantially parallel to the occlusal of the arch. While the diameter of this lumen may be of any suitable size, it is preferably about 0.020 inch so that it may easily accommodate uprighting wires up to 0.018 inch in diameter. A round uprighting wire 38 is illustrated, as seen most clearly in FIGS. 3 and 4, directly behind the main archwire 23 in the main archwire slot and is generally referred to as an uprighting wire. It will be understood that a small wire having a polygonal cross section could be used as long as the wire is free to rotate along its length in the lumen or slot. Thus, the wire is sized to fit loosely in the lumen or slot. Initially, in the final stage of treatment it can be appreciated that a relatively small, round archwire of super-elastic material that is 0.014 inch or less in diameter could be used and that later when additional control is desired, super-elastic wires having a diameter of 0.016 or 0.018 inch could be used. A suitable super-elastic wire could be a nickel titanium wire. Further, where increased uprighting forces are desired, a higher tensile stainless steel uprighting wire may be used.

The uprighting wire 38 is preferably continuous along the brackets of the system and travels from the molar on one side of the arch to the molar on the other or opposing side, although it could be segmented if desired. To facilitate insertion, the uprighting wires could also be sectional or segmented with more than one applied to a dental arch at one time.

When moving into the final stage of treatment, the uprighting wire 38 can be mounted by inserting both ends at the midline into the mesial openings of the horizontal tunnels or tubes of the central incisor brackets and then threaded through the other brackets so that it terminates mesial to the molar tubes on the molar teeth. As illustrated in FIG. 5, the super-elastic wire 38 is continuous and threaded through a series of brackets 10a, 10b, 10c and 10d and terminating short of the tube 42. If desired, an additional tube or a multi-tube appliance can be provided on the molar so that the uprighting wire can also deliver or receive forces from the molar.

Subsequent to the placement of the uprighting wire 38, the main archwire 23 is placed in the usual manner in the main archwire slots 22 of the brackets as well as molar buccal tubes 42. The main archwire 23 is preferably retained on the brackets with elastomeric rings or ligatures (not shown) although any suitable means may be used. In self-ligating brackets, caps are provided to retain the archwire in the archwire slot. The patient can then be dismissed for approximately three to four months and the progress of the uprighting functions will be evaluated at the next visit. In the absence of damage to the system, there should then be no need for further adjustments, as all of the teeth will have been moved to their ideal final upright positions, as shown by the brackets illustrated in FIG. 6. At that time, it will be appreciated that the fixed appliances can be removed and appropriate retainers placed with the patient.

The appliance in the further embodiments of FIGS. 7 to 14 are illustrated as applied to an upper right cuspid tooth. Further, these brackets include the usual vertical opening lingual to the archwire slot for receiving the tail of a rotating spring or an uprighting spring when early individual tipping correction is desired. With respect to the brackets shown in FIGS. 8 to 14, the bonding bases or pads have been removed, and the brackets are seen from the lingual for clarity in describing the lumens and the function of the brackets.

Referring now to the embodiment of FIGS. 7 and 8, a modified bracket 50 is shown mounted on a bonding base or pad 51 and the base is removed from the bracket in FIG. 8 so that the shape and construction and function of the tunnels, lumens or openings may be easily viewed. This embodiment differentiates from the embodiment of FIGS. 1 to 6 in that the tunnel while segmented is also formed to facilitate the threading of the uprighting wire. The tunnel, generally designated by the numeral 54, is defined by spaced apart uprighting wire guide members 55 and 56 and 57 and 58. Members 55 and 57 are gingivally located, while members 56 and 58 are occlusally located. Opposed members 55 and 56 are disposed at the mesial side of the bracket, while opposed members 57 and 58 are disposed at the distal side of the bracket. The members 55 and 56, respectively, include upper and lower or gingival and occlusal flat surfaces 55a and 56a, while the members 57 and 58 similarly include upper and lower or gingival and occlusal flat surfaces 57a and 58a. These surfaces and an axis extending between the members parallel the horizontal axis of the bracket as depicted by the line 60 which also is coincident with the horizontal axis of the main archwire slot defined by the flat surfaces. The members 55 and 56 further include beveled or flared surfaces 55b and 56b at the mesial side of the bracket to facilitate the threading of the uprighting wire into the bracket. Similarly, if the uprighting wire is to be threaded from the distal side of the bracket, flared or beveled surfaces 57b and 58b are provided to facilitate the threading operation. Similarly, the wire inlets to the openings near the center of the bracket defined by members 57 and 58, and 55 and 56 are beveled or flared to guide the leading end of a wire between the openings defined by the guide members as the uprighting wire is threaded through the appliance uprighting lumen.

The bracket 50 also includes a vertically extending opening or slot 59 that cuts through the lumen or opening 54, and is used for receiving the tail of a rotating spring to apply rotating forces to a malrotated tooth where needed. It may also be used for an uprighting spring during treatment before placement of the uprighting wire. While it is preferred to include the vertical opening, it should be appreciated it is not necessary for the present invention, and none are shown in the embodiment of FIGS. 1 to 6. Further, the uprighting wire 38 will apply some rotating forces.

The appliance embodiment of FIG. 9, generally designated by the numeral 62, differentiates from the embodiment of FIGS. 7 and 8 in that the axis of the segmented tunnel is mesial distally angularly offset from the horizontal axis of the bracket so that the uprighting wire maintains a positive force on the bracket once the bracket/tooth is uprighted. The tunnel, generally indicated by the numeral 63, is defined by a pair of opposed gingival and occlusal uprighting wire guide members 64, 65 at the mesial side of the bracket and a pair of gingival and occlusal uprighting guide members 66, 67 at the distal side of the bracket. The flat surfaces of the members 64 and 65 are designated 64a and 65a, while the flat surfaces of the members 66 and 67 are designated 66a and 67a. Collectively, the members 64–65 and 66–67 define a guided path for the uprighting wire. These flat surfaces parallel the axis 69 which is offset along a mesial distal plane from the horizontal axis 60 of the bracket and the archwire slot to maintain a positive force on the appliance once the appliance/tooth is uprighted when the energy of the uprighting wire is applied to the bracket. Because the tunnel is offset, the forces applied by the uprighting wire would produce a greater uprighting force during any degree of tipping. The amount of offset may vary from two to fifteen degrees depending on the amount of additional force required from the uprighting wire to produce an adequate positive force. Additionally, the forces applied by the energy of the wire would not drop to zero but remain active and positive even when the tooth/bracket has reached its final pre-adjusted tip and torque angulations. As in the embodiment of FIGS. 7 and 8, the inlets and outlets to the openings defined by each set of opposed uprighting wire guide members are flared to assist in guiding the uprighting wire through the lumen.

It will be appreciated that the use of extremely thin flexible uprighting wires would overcome the difficulty in threading between severely tipped teeth, and this angular embodiment could be particularly used in connection with the application of forces to upper anterior teeth, particularly the central and lateral incisors which tip less and require early and energetic uprighting forces to provide the desired torque changes in the shortest possible time.

A modification of the bracket of FIG. 8 is shown in FIG. 10 and generally indicated by the numeral 70 and which differs from the embodiment of FIG. 8 in the formation of the surfaces engageable by the uprighting wire in the tunnel. The bracket 70 includes a segmented tunnel 72 formed by spaced apart pairs of gingival and occlusal uprighting wire guide members 74, 75 and 76, 77. Each of these members are V-shaped or inverted V-shaped to provide a knife-like edge contacting surface that includes edges 74a, 75a, 76a, 77a and inclined surfaces 74b, 75b, 74c and 75c and 76b, 77b, 76c and 77c. The edges of the opposing members provide edge contact with the uprighting wire as it is threaded through the tunnel 72. Because of the inclined surfaces to the inlets and outlets of the openings defined by the members 74–75 and 76–77, the openings are automatically flared to enhance the guiding of the uprighting wire through the lumen.

A further embodiment of the invention is shown in FIG. 11 and generally designated by the numeral 80 which differs from the embodiments of FIGS. 8 and 10 in that each pair of tunnel or lumen forming uprighting wire guide members include an opposed flat surface member and a knife-edge member to define the contact surfaces for the uprighting wire. In this respect, the bracket 80 includes opposed members 82 and 83 on one end of the bracket and opposed members 84 and 85 on the other end of the bracket. The members 82 and 85 are diagonally opposed and both include a knife-edge against which the flexed uprighting wire 90 contacts, as shown in FIG. 11, to produce a force in the direction of arrow 92. The rigid main archwire 93 is shown in dotted lines to show the relationship between the normal position of the main archwire when the tooth is tipped and the ability of the uprighting wire 90 to upright the tooth and bring the torquing surface of the main archwire slot into engagement with the main archwire. FIG. 11 illustrates the bracket/tooth in its initial tipped position with the uprighting wire 90 flexed to deliver the required uprighting forces.

A further embodiment of the invention is shown in FIGS. 12 to 14. These figures, which are lingual views of the upper right cuspid brackets with the bonding pads removed for purposes of illustrating and explaining the invention, also illustrate the methodology of threading the uprighting wire during treatment of a patient having a severely tipped tooth as is often found with canines. FIG. 12 shows the tooth/bracket in severely tipped relation, while FIG. 13 shows the tooth/bracket in partially uprighted position, and FIG. 14 shows the tooth/bracket in fully upright position. The exiting lumen or opening for the uprighting wire used in the initial stage in this embodiment is disposed incisally to facilitate the threading of the uprighting wire and thereafter changed in the later stages to a gingival lumen that reactivates the uprighting wire to complete uprighting and continue delivering an uprighting force even after the tooth/bracket is in the fully uprighted position as limited by the main archwire slot until a time when the appliance is removed from the tooth.

The bracket, generally designated by the numeral 96, illustrates the usage for an upper right canine and includes an inlet lumen or opening 98 at the mesial side of the bracket and through which the uprighting wire 90 is initially threaded. This lumen 98 is defined by gingival and occlusal uprighting wire guide members 100 and 102. While the horizontal axis of this bracket generally runs through the central area defined by the guide members 100 and 102, the central area between the gingival and occlusal uprighting wire guide members 104 and 106 at the distal side of the bracket are lower than the horizontal axis, as seen particularly in FIG. 14 and which defines an incisal exiting lumen 98a. Thus, the lower or incisal lumen 98a through which the uprighting wire 90 is exited, as seen in FIG. 12, is provided to overcome the difficulty of threading an uprighting wire through a bracket on a severely tipped tooth. Thus, less flexing of the wire will be required to thread the wire through lumen 98a.

When the tooth/bracket is partially uprighted, as in FIG. 13, from the position of FIG. 12 and shown in phantom in FIG. 13, a stronger uprighting force can then be applied to the tooth/bracket to continue uprighting in the direction of the arrow 112 by rethreading the uprighting wire so that the wire exits the bracket through the upper or gingival lumen or opening 110, wherein the wire passes over the top of the gingival uprighting wire guide member 104, as seen in FIGS. 13 and 14. In FIG. 12, the flexed uprighting wire is in contact with the gingival member 100 and the occlusal member 106, while in FIG. 13 the flexed uprighting wire is in contact with the gingival member 100 and the gingival side of the gingival member 104.

The uprighting wire is maintained in the upper or gingival opening or lumen 110 through the remaining part of the treatment of the patient to effect full uprighting of the tooth/bracket to the position shown in solid lines in FIG. 14.

Also shown in FIG. 14 in phantom is the position of the bracket as shown in solid lines in FIG. 13 and from which the bracket moves to the final position shown in solid lines. Thus, the finally uprighted position, as shown in FIG. 14, is maintained by the uprighting wire as threaded Through the upper lumen wherein the wire remains flexed to positively apply a force to the tooth/bracket at the uprighted position when the stops engage the main archwire in the main archwire slot, as can be accomplished by the embodiment of FIG. 9. In the event the tooth is not severely tipped in the first instance, the uprighting wire could be initially threaded through the upper or gingival lumen, as shown in FIGS. 13 and 14. While an uprighting wire of the same size could be used throughout treatment, it should be appreciated that a larger size wire may be used at any time and particularly when uprighting has been completed and it is desired to be maintained for a period of time.

While the preferred position of the uprighting wire according to the present invention is lingual to the main archwire as in the embodiment of FIGS. 1 to 14, it will be appreciated that the lumen or opening for the uprighting wire may be positioned incisally or gingivally of the main archwire slot, as illustrated in the embodiment of FIG. 15. In this embodiment the bracket is generally designated by the numeral 114 in mounted relation on a tooth 116 and which includes a main archwire slot 118. Shown in phantom are, respectively, continuous incisal or gingival uprighting wire guide openings or lumens 120 and 122 that are, respectively, incisally or gingivally positioned relative to the main archwire slot 118. It should be appreciated that a bracket may be provided with one or the other of such lumens or with both lumens if desired to provide an option as to where the uprighting wire would be placed. In this embodiment it would not be necessary to remove the main archwire when an uprighting wire is threaded through the brackets of the mouth due to the positions of the lumens or openings for an uprighting wire. These lumens may extend parallel to or at an incline to the horizontal axis of the archwire slot while otherwise being in alignment with the slot.

The embodiment of FIG. 16 differs from the embodiment of FIG. 15 in that an, uprighting wire riding slot is formed in the face of the bracket instead of an uprighting lumen. This bracket, generally designated by the numeral 128, includes an uprighting slot 130 that may be parallel to or at an incline to the horizontal axis of the main archwire slot. While the slot is square in shape, it could be rounded. Further, while the slot is shown in the gingival wing, it could be disposed in the incisal wing. A suitable ligature or cap would be used to retain an uprighting wire in the uprighting slot as well as a larger stiffer wire in the archwire slot.

In view of the foregoing, it will be appreciated that the appliance of the invention is an improved appliance that allows tipping, limits uprighting and controls torquing, while also producing final axial control without using uprighting springs. The improved appliance of the invention makes it impossible to apply the wrong uprighting forces sometimes caused by improperly mounting an uprighting spring in the final treatment stage, enhances the comfort, hygienics, and aesthetics of a patient, and thereby can also reduce the number of visits and total treatment time for a patient.

It will be understood that modifications and variations may be effected without departing from the scope of the novel concepts of the present invention, but it is understood that this application is to be limited only by the scope of the appended claims.

The invention is hereby claimed as follows:

1. An orthodontic bracket comprising:
   a horizontally opening archwire slot adapted to receive a main aligning archwire, said slot including means coacting with said archwire to allow crown tipping, limit root uprighting to a predetermined angulation, and control torquing, and
   a mesiodistally extending tunnel or lumen separate from said slot for receiving a relatively small uprighting wire adapted to apply an uprighting force to the bracket.

2. The orthodontic bracket of claim 1, wherein the lumen is sized to allow a loose fit with the wire.

3. The orthodontic bracket of claim 1, wherein said uprighting wire is continuous.

4. The bracket of claim 3, wherein said lumen is directly lingual to said archwire slot.

5. The orthodontic bracket of claim 1, wherein said uprighting wire is segmented.

6. The orthodontic bracket of claim 1, wherein the uprighting wire is of super-elastic material.

7. The orthodontic bracket of claim 1, wherein the uprighting wire is of high-tensile material.

8. In an orthodontic system for applying corrective forces to teeth of an arch including centrals, laterals, cuspids, and bicuspids, orthodontic appliances on the centrals, laterals, cuspids, and bicuspids, each appliance including a horizontally opening archwire slot having means for permitting crown tipping, limit root uprighting and torquing, and a substantially passive rectangular or square archwire in said slots, the improvement in the appliances which comprise:
   each appliance including a mesiodistally extending tunnel separate from the archwire slot, and a relatively small uprighting wire extending through the tunnels of said appliances for applying uprighting forces to the appliances, whereby the need fix individual uprighting springs is eliminated.

9. The orthodontic system of claim 8, wherein said uprighting wire is continuous.

10. The orthodontic system of claim 8, wherein said uprighting wire is segmented.

11. The orthodontic system of claim 8, wherein said tunnels are aligned with said archwire slots and the occlusal plane of the teeth on which the appliances are mounted.

12. The orthodontic system of claim 11, wherein the tunnels are lingual to said archwire slots.

13. The orthodontic system of claim 12, wherein the uprighting wire terminates at each end mesial to the molars.

14. In an orthodontic system for applying corrective forces to teeth of an arch including centrals, laterals, cuspids, and bicuspids brackets on the centrals, laterals, cuspids, and bicuspids, each bracket including a horizontally extending archwire slot having means for permitting crown tipping, limit root uprighting and torquing, and a substantially passive rectangular or square archwire in the slots, the improvement m the brackets which comprise:
   mesiodistally extending tunnels in said brackets separate from the archwire slots, and a relatively small uprighting wire extending through the tunnels for applying uprighting forces to the brackets, whereby the need for uprighting springs is eliminated for final positioning.

15. An orthodontic appliance having a labial face and adapted to be mounted on a tooth, said appliance comprising:
   a horizontally opening archwire slot adapted to receive a main archwire, said slot including means coacting with said archwire to allow crown tipping, limit root uprighting to a predetermined angulation, and control torquing, and means extending mesiodistally of said appliance for receiving an uprighting wire and guiding the wire trough the appliance to apply an uprighting force to the appliance, wherein said wire receiving means is disposed adjacent to but separate from said archwire slot.

16. The orthodontic appliance of claim 15, wherein said uprighting wire receiving means is a generally horizontally extending lumen or tunnel.

17. The orthodontic appliance of claim 16, wherein said lumen or tunnel extends generally horizontally.

18. The orthodontic appliance of claim 16, wherein said lumen is continuous.

19. The orthodontic appliance of claim 16, wherein said lumen is segmented.

20. The orthodontic appliance of claim 16, wherein said lumen includes a flared portion at least at one end to facilitate the initial guiding of a wire into said end.

21. The orthodontic appliance of claim 16, wherein said lumen includes a flared portion at both ends to facilitate the Initial guiding of a wire into either end.

22. The orthodontic appliance of claim 16, wherein said lumen includes a plurality of opposed upper and lower flat surfaces extending parallel to each other and parallel to a horizontal axis running through said archwire slot.

23. The orthodontic appliance of claim 16, wherein said lumen includes a plurality of opposed upper and lower substantially flat surfaces extending parallel to each other and defining a lumen path angularly offset from a horizontal axis running through said archwire slot.

24. The orthodontic appliance of claim 16, wherein said lumen includes a plurality of opposed upper and lower substantially knife-shaped edges.

25. The orthodontic appliance of claim 16, wherein said lumen includes a plurality of opposed upper and lower wire guiding surfaces and/or edges.

26. The orthodontic, appliance of claim 25, wherein said wire guiding surfaces and/or edges include both flat surfaces and substantially knife-shaped edges.

27. The orthodontic appliance of claim 26, wherein the opposed surfaces and/or knife-shaped edges may be like or mixed in opposing relation.

28. The orthodontic appliance of claim 16, wherein the lumen is positioned lingual to the archwire slot.

29. The orthodontic appliance of claim 16, wherein the lumen is positioned incisally to the archwire slot.

30. The orthodontic appliance of claim 16, wherein the lumen is positioned gingivally to the archwire slot.

31. The orthodontic appliance of claim 16, wherein the axis of the lumen is labiolingually aligned with said archwire slot.

32. The orthodontic appliance of claim 16, wherein the axis of the lumen is occlusogingivally aligned with said archwire slot.

33. The orthodontic appliance of claim 16, wherein the axis of the lumen is angularly offset from the axis of the archwire slot such that the uprighting wire maintains a positive force on the appliance once the appliance/tooth is uprighted.

34. The orthodontic appliance of claim 16, wherein said lumen includes a pair of opposed gingival and occlusal uprighting wire guide members atone of the mesial or distal ends of the lumen and a second pair of opposed gingival and occlusal uprighting wire guide members at the other of the mesial or distal ends of the lumen defining a path for the uprighting wire extending between both said pair of guide members.

35. The orthodontic appliance of claim 16, wherein said lumen includes a first pair of opposed gingival and occlusal uprighting wire guide members at one of the mesial or distal ends of the lumen and a second pair of opposed gingival and occlusal, uprighting wire guide members at the other of the mesial or distal ends of the lumen defining a first path for the uprighting wire extending between both said pair of guide members which requires less flexing of the uprighting wires and a second path extending between said first pair of guide members and over the upper side of the gingival guide member of said second pair of guide members for maintaining a positive uprighting force on said appliance after it is uprighted.

36. The orthodontic appliance of claim 15, wherein said uprighting wire receiving means is an uprighting slot disposed in the labial face of the appliance.

37. The orthodontic appliance of claim 36, wherein said uprighting slot is disposed gingivally to said archwire slot.

38. The orthodontic appliance of claim 36, wherein said uprighting slot is disposed occlusally to said archwire slot.

39. The orthodontic appliance of claim 38, wherein said uprighting slot is angularly offset from the horizontal axis of the archwire slot.

40. The orthodontic appliance of claim 37, wherein said uprighting slot is angularly offset from the horizontal axis of the archwire slot.

41. The orthodontic appliance of claim 15, wherein said uprighting wire receiving means includes at least one guide member at the mesial or distal side of the appliance defining two paths for the uprighting wire.

* * * * *

UNITED STATES PATENT AND TRADEMARK OFFICE
CERTIFICATE OF CORRECTION

PATENT NO. : 6,682,345 B2
DATED : January 27, 2004
INVENTOR(S) : Christopher K. Kesling, Peter C. Kesling and Richard C. Parkhouse It is certified that error appears in the above-identified patent and that said Letters Patent is hereby corrected as shown below:

Column 2,
Line 24, change "wit" to -- with --;

Column 9,
Line 40, after "an" delete the comma ",", change "riding" to -- guiding --;

Column 10,
Line 49, after "bicuspids" insert a comma -- , --;

Column 12,
Line 12, change "atone" to -- at one --;
Line 22, after "occlusal" delete the comma ",";
Line 26, change "wires" to -- wire, --.

Signed and Sealed this

Twenty-second Day of June, 2004

JON W. DUDAS
*Acting Director of the United States Patent and Trademark Office*

UNITED STATES PATENT AND TRADEMARK OFFICE
CERTIFICATE OF CORRECTION

| | |
|---|---|
| PATENT NO. | : 6,682,345 B2 |
| APPLICATION NO. | : 10/177951 |
| DATED | : January 27, 2004 |
| INVENTOR(S) | : Christopher K. Kesling, Peter C. Kesling and Richard C. Parkhouse |

Page 1 of 1

It is certified that error appears in the above-identified patent and that said Letters Patent is hereby corrected as shown below:

Column 3, line 52, change "uprigining" to --uprighting--.

Signed and Sealed this

Fifteenth Day of January, 2008

JON W. DUDAS
*Director of the United States Patent and Trademark Office*